(12) United States Patent
Balkus, Jr. et al.

(10) Patent No.: US 9,017,653 B2
(45) Date of Patent: Apr. 28, 2015

(54) NITRIC OXIDE-RELEASING COMPOSITIONS AND METHODS

(71) Applicant: The Board of Regents of the University of Texas System, Austin, TX (US)

(72) Inventors: Kenneth J. Balkus, Jr., The Colony, TX (US); Wenjin Deng, St. Louis, MO (US); Alysia Lowe, Dallas, TX (US); Dennis W. Smith, Jr., The Colony, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 13/918,688

(22) Filed: Jun. 14, 2013

(65) Prior Publication Data

US 2013/0337033 A1     Dec. 19, 2013

Related U.S. Application Data

(60) Provisional application No. 61/659,890, filed on Jun. 14, 2012, provisional application No. 61/742,625, filed on Nov. 9, 2012.

(51) Int. Cl.
| | | |
|---|---|---|
| A61K 31/74 | (2006.01) |
| A61K 31/787 | (2006.01) |
| A61K 9/70 | (2006.01) |
| C08F 226/06 | (2006.01) |
| C08F 220/48 | (2006.01) |
| A61L 15/24 | (2006.01) |
| A61L 15/44 | (2006.01) |
| A61L 15/64 | (2006.01) |
| A61L 17/00 | (2006.01) |
| A61L 17/10 | (2006.01) |
| A61L 17/14 | (2006.01) |
| C08F 220/44 | (2006.01) |

(52) U.S. Cl.
CPC ............. *A61K 31/787* (2013.01); *A61K 9/70* (2013.01); *C08F 226/06* (2013.01); *C08F 220/48* (2013.01); *A61L 15/24* (2013.01); *A61L 15/44* (2013.01); *A61L 15/64* (2013.01); *A61L 17/005* (2013.01); *A61L 17/10* (2013.01); *A61L 17/145* (2013.01); *C08F 220/44* (2013.01); *A61L 2300/114* (2013.01)

(58) Field of Classification Search
CPC ..................................................... A61K 31/04
See application file for complete search history.

(56) References Cited

U.S. PATENT DOCUMENTS 7,968,664 B2   6/2011   Hrabie et al.

FOREIGN PATENT DOCUMENTS

WO   WO 2006037105 A2 *   4/2006

OTHER PUBLICATIONS

Pekel et al, Synthesis and Characterization of Poly(N-vinylimidazole-co-acrylonitrile) and Determination of Monomer Reactivity Ratios, Macromolecular Chemistry and Physics, 2004, 205(8), 1088-1095.*

* cited by examiner

*Primary Examiner* — Paul Dickinson
(74) *Attorney, Agent, or Firm* — Saliwanchik, Lloyd & Eisenschenk (57) ABSTRACT

The invention relates to nitric oxide-releasing compositions comprising polyacrylonitrile polymers that are diazeniumdiolated, and to medical devices comprising such compositions, as well as to methods of making and using the compositions and medical devices.

16 Claims, 5 Drawing Sheets

NITRIC OXIDE-RELEASING COMPOSITIONS AND METHODS

CROSS-REFERENCES TO RELATED APPLICATIONS

This application claims the benefit of U.S. Provisional Application No. 61/659,890, filed Jun. 14, 2012 and U.S. Provisional Application No. 61/724,625 filed Nov. 9, 2012, each of which is incorporated by reference as if fully set forth herein.

FIELD OF THE INVENTION

The invention relates to nitric oxide-releasing compositions comprising polyacrylonitrile polymers that are diazeniumdiolated, and to medical devices comprising such compositions, as well as to methods of making and using the compositions and medical devices.

BACKGROUND OF THE INVENTION

The development and introduction of surgical materials is a growing field of research, and the biocompatibility of device materials can influence the outcome of a surgery. Medical devices that come into contact with blood are prone to cause damage, leading to conditions such as thrombosis and platelet aggregation. For example, balloon inflation during angioplasty can damage the endothelial lining in cells, which causes blood vessels to narrow, restricting blood flow. Recurrence of this condition leads to restenosis. Anticoagulants can be prescribed in conjunction with the use of blood contacting devices to reduce the chance of blood damage. However, continual use leads to side effects, including greater chance of hemorrhaging. Not only can devices cause issues for the patient, but the device's clinical performance can be affected. If a device were thromboresistant, these issues would be relieved. Due to its discovery as an inhibitor of platelet aggregation, nitric oxide (NO) has become a widely studied molecule for polymeric materials in biomedical applications.

Nitric Oxide (NO) is a molecule that is produced naturally in the body through enzymatic processes. NO aids in several functions in the body, including wound healing. It is produced during the inflammatory and proliferative phases of wound healing, and is used by the body to transition from the first to the second phase. One of the functions of NO in wound healing is that it acts as a vasodilator, widening blood vessels and helping blood to flow in body tissue. Not only does NO aid in healing, but it also serves as an antibacterial agent. This could be beneficial to all phases of the wound healing process. When incorporating NO into medical devices, the number of complications from wounds resulting from surgical procedures, diabetic lesions, burns and cancer, could potentially decrease.

For the effects of NO delivery to be positive, an appropriate concentration of the drug must be administered. A coating on the polymer will enable a controlled release of NO into the biological system. This coating improves stability; preventing NO from spontaneously releasing from the polymer. It can also allow higher storage retention.

Furthermore, nitric oxide plays an important role in several physiological functions, including immune responses, blood clotting, vasodilation, pulmonary hypertension, and neurotransmission. By incorporating NO into surgical materials, prevention from infections and enhanced wound healing would be possible. Synthesized in the body by nitric oxide synthase (NOS), oxygen reacts with the amino acid L-arginine to produce NO and L-citrulline. NO has been shown to be an antimicrobial agent. NO is produced initially at a higher concentration, to clear out bacterial infection, and then held at lower concentrations, to allow for the wound healing process to begin. It has been shown in the literature that application of NO to wounds can promote the healing process. This process occurs due to the fact that NO is also the endothelium derived relaxing factor. Upon NOS activation, NO signals smooth muscle to relax, causing vasodilation of blood vessels to occur. While NO also inhibits platelet aggregation and inflammatory cell activation, it can be applied as a thromboresistant molecule capable of enhanced wound healing purposes when incorporated into polymer surgical materials.

Due to its capability to prevent inflammation and increase blood flow, storage and delivery of nitric oxide has recently become extensively studied for biological purposes. Several classes of NO donor molecules exist, these include organic nitrates, organic nitrites, metal-NO complexes, nitrosamines, nitrosamines, nitrosothiols, and furoxans. A special class of NO adducts are the diazeniumdiolates, or NONOates. Diazeniumdiolates are desirable due to their general stability, and ability to spontaneously release NO at physiological temperature and pH. Diazeniumdiolates, which contain the [N(O)NO]-functional group, release two molar equivalents of NO, with half-lives ranging from 2 seconds to 20 hours. The 2 moles of NO are generally released by a proton source such as humidity or acids, and can also be released by heat or photolysis.

Polyacrylonitrile (PAN) is an important material for producing carbon fibers, and used in many applications, largely in the sporting goods and aerospace industries. Native PAN does not bind NO. After undergoing stabilization, however, the α-hydrogen on the cyano group becomes more acidic and allows NO to bind. In the stabilization process, PAN is treated thermally to allow for the cyano groups to undergo intramolecular nitrile reaction. Formation of the diazeniumdiolate group on PAN has also been achieved using a strong base for stabilization. Some of the disadvantages associated with thermally treated and strong base-treated include the inability to further manipulate the compositions derived from these methods to form medical devices or other useful objects that can release NO. Therefore, it would be desirable to develop compositions comprising PAN that can bind NO without the requirement for heat treatment or treatment with strong bases.

SUMMARY OF THE INVENTION

The invention provides nitric oxide-releasing compositions comprising polyacrylonitrile polymers that are diazeniumdiolated. The polymers of the invention are co-polymers comprising acrylonitrile (AN) and other suitable monomers such as 1-vinylimidazole (VIM). The polymers of the invention also include ter-polymers comprising AN, VIM and an olefinic monomer containing a >C=C< group. The diazeniumdiolated acrylonitrile polymers can be used in medical devices. The invention also provides compositions and medical devices comprising such diazeniumdiolated PAN polymers and methods of using such compositions and devices.

DETAILED DESCRIPTION OF EXEMPLARY EMBODIMENTS

The invention provides acrylonitrile containing polymers that are capable of releasing nitric oxide. The invention also provides compositions comprising acrylonitrile containing polymers that are capable of releasing nitric oxide and medical devices that comprise these compositions. The polymers, compositions and medical devices which include the polymers are useful for treating medical conditions where a release of nitric oxide is beneficial.

An embodiment of the invention provides a nitric oxide-releasing acrylonitrile containing co-polymer comprising 1-vinylimidazole (VIM) and at least one nitric oxide releasing $N_2O_2^-$ group that is directly attached to the copolymer backbone. In another embodiment of the invention, a nitric oxide-releasing acrylonitrile containing ter-polymer comprising 1-vinylimidazole (VIM) and a monomer containing a >C=C< group (olefin) and at least one nitric oxide releasing $N_2O_2^-$ group that is directly attached to the terpolymer backbone. In accordance with embodiments of the invention, the acrylonitrile co-polymer and terpolymer backbones can be diazeniumdiolated with one or more $N_2O_2^-$ groups. In certain embodiments of the invention, the $N_2O_2^-$ group binds to the carbon backbone of the AN monomer in the claimed polymer. In other embodiments, the $N_2O_2^-$ group binds to the carbon backbone of the co-monomer (such as VIM or BA) in the claimed polymer.

PAN is a vinyl polymer which is prepared from acrylonitrile typically via free radical vinyl polymerization. Other polymerization conditions can be used to prepare isotactic, syndiotactic, or a combination of all three configurations. In general, PAN is used to make materials such as carbon fiber.

The co-monomers in the acrylonitrile copolymer and terpolymer can be present in any suitable ratio in the copolymer. For example, if two monomers, A and B, are used, the resulting copolymer can have a range of weight ratios of A:B, such that the total of the monomers adds up to 100%. In certain embodiments of the invention, the amounts of each monomer in a copolymer varies from 1 wt % to 99 wt %. More preferably, the amounts of each monomer may be present in the copolymer within a range 10 wt % to 90 wt %, 20 wt % to 80 wt %, 30 wt % to 70 wt %, 40 wt % to 60 wt % or 50 wt %.

In the case of a ter-polymer having monomers A, B and C, the resulting terpolymer can have a range of weight ratios of A:B:C such that the total of the monomers adds up to 100%. In certain embodiments of the invention, the amounts of each monomer in a terpolymer varies from 1 wt % to 99 wt %. More preferably, the amounts of each monomer may be present in the copolymer within a range 10 wt % to 90 wt %, 20 wt % to 80 wt %, 30 wt % to 70 wt %, 40 wt % to 60 wt % or 50 wt %.

In certain embodiments of the invention, the polymers of the claimed invention comprise a monomer containing a >C=C< group. In another embodiment of the invention, the polymers of the claimed invention comprise a monomer containing a >C=C< group wherein the monomer containing the >C=C< group is capable of binding NO. In other embodiments of the invention, the polymers of the claimed invention comprise a monomer containing a >C=C< group wherein the monomer containing the >C=C< group binds NO.

In certain embodiments of the invention, the monomer containing a >C=C< group is selected from 1-vinyl imidazole, 4-vinyl imidazole, 2-vinyl imidazole, 1-methyl-2-vinyl imidazole; acrylate including, methyl acrylate, ethyl acrylate, and butyl acrylate, methacrylate including methyl methacrylate and butyl methacrylate, acrylic hydroxyl, methacrylic hydroxyl; diene including isoprene, and butadiene; ethylene and propylene.

In an embodiment of the invention, a co-polymer of AN and VIM is formed by introducing VIM into PAN using a polymerization process. VIM co-monomer is introduced to enhance the α-hydrogen acidity of PAN and help it to bind NO and decrease crystallinity of PAN allowing melt-processability. Additionally, VIM is capable of binding NO and has been shown to bind NO.

In other embodiments of the invention, AN-based terpolymers, such as AN/VIM/isoprene (IP), AN/VIM/butyl acrylate (BA), AN/VIM/ethylene, AN/VIM/butadiene, and AN/VIM/3,4-dimethoxystyrene are formed using a polymerization process. The polymerization process can be carried out any known method. In certain embodiments, the polymerization process is carried out using a free radical polymerization process.

The invention provides medical devices which are capable of releasing nitric oxide when in use, but which are otherwise inert to nitric oxide release. In particular, NO-releasing functional groups are bound to an acrylonitrile containing polymer comprising at least one diazeniumdiolate group which, in turn, is coated on a substrate. Alternatively, the diazeniumdiolated acrylonitrile-containing polymer can form the medical device itself.

A "medical device" includes any device having surfaces that contact tissue, blood, or other bodily fluids in the course of their use or operation, which are found on or are subsequently used within a mammal. Medical devices include endoprostheses implanted in a mammal (e.g., a human), such as vascular grafts, stents, pacemaker leads, surgical prosthetic conduits, heart valves, and the like, that are implanted in blood vessels or the heart. Medical devices also include devices for temporary intravascular use such as catheters, guide wires, amniocentesis and biopsy needles, cannulae, drainage tubes, shunts, sensors, transducers, probes and the like which are placed into the blood vessels, the heart, organs or tissues for purposes of monitoring or repair or treatment. Medical devices also include prostheses such as artificial joints such as hips or knees as well as artificial hearts. In addition, medical devices include sutures, hemostats used in surgery, textile fabrics made from the polymers, antimicrobial materials, surgical mesh, transdermal patches, and wound dressings/bandages.

In accordance with embodiments of the invention, the acrylonitrile-based fibers can store and release nitric oxide (NO) and be used for wound healing, as a type of bandage or gauze.

The major component of the bandage material is acrylonitrile (AN). AN is polymerized with other monomer(s) to form a copolymer, including but not limited to, 1-vinyl imidazole, butyl acrylate, isoprene, or butadiene monomers. In certain embodiments of the invention, the AN co-polymer comprises a biodegradable monomer(s) such as caprolactam, lactide or glycolide. These bandages can be electrospun. They could also be coated with a biodegradable polymer to control the release rate of NO. The coating materials are biodegradable polymers, including but not limited to polyglycolide, polylactide, polycaprolactone poly (lactic-co-glycolide acid), poly (glycolide-co-caprolactone), and poly (glycolide-co-trimethylene carbonate). The purpose behind the selection of a particular polymer relates to the different mechanical properties and release characteristics possessed by the selected polymer.

In embodiments of the invention, the polymers of the claimed invention are used to create fibers using a spinning process. The spinning process can use either electrospinning or melt spinning methods. Electrospinning is a technique which uses electrical charge to draw a polymer solution from a spinneret. The solution is ejected toward a rotating drum which is grounded. The solution evaporates, which results in a non-woven sheet of fibers which resembles a bandage or gauze. Fiber diameter can be controlled by spinneret size and distance from the spinneret to the grounded collector. Bandage thickness can be controlled by spinning duration. Furthermore, electrospinning can affect chain alignment and packing of the polymer fibers, which in turn affects the mechanical properties and NO binding of the electrospun sheets. The properties exhibited by the electrospun sheets are improved relative bulk powders, films or wet/melt spun fibers.

A melt-spinning process is advantageous over conventional solution spinning because it eliminates the use of toxic solvent. Furthermore, the recovery of melt-spun fibers also makes melt-spinning a more cost effective method. This process also uses a more concentrated precursor which creates fibers that are essentially void-free.

Bandage and gauze materials can be prepared from fibers spun from acrylonitrile-based co- and ter-polymers, such as vinylimidazole, butyl acrylate, isoprene, butadiene, and caprolactam. Once the polymer is spun into fibers, it is exposed to high pressure of NO, allowing the formation of a NO molecular donor group, a diazeniumdiolate (NONOate). These NONOates release two molar equivalents of NO spontaneously upon exposure to physiological conditions. The resulting bandages are used for wound healing and other therapeutics uses.

In certain embodiments of the invention, it is possible for the fibers created from the polymers to be used a suture. The fibers can be used as a monofilament suture, with or without a coating, or as a multifilament suture, braided or twisted with another suture material. In certain embodiments of the invention, the sutures prepared from fibers of the polymers of the claimed invention are twisted or braided with commercially available fibers for improved toughness.

In certain embodiments of the invention, the polymers of the claimed invention are combined with a crosslinking compound prior to being spun into fibers. In an embodiment of the invention, the crosslinking compound is azobisisobutyronitrile (AIBN). The AIBN compound is used to crosslink the polymer and modify the physical properties of the spun fibers. For example, fibers spun with AIBN are less sticky.

Figure 1:
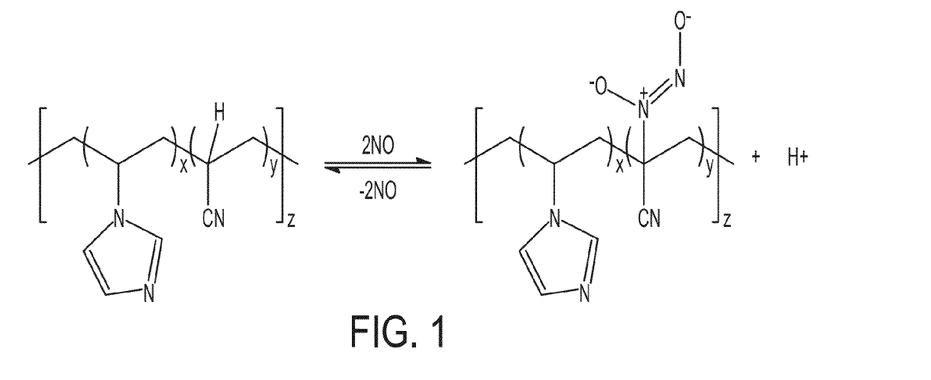
FIG. 1 shows the reversible binding and release of NO on a AN/VIM copolymer composition in accordance with an embodiment of the invention.
Figure 2:
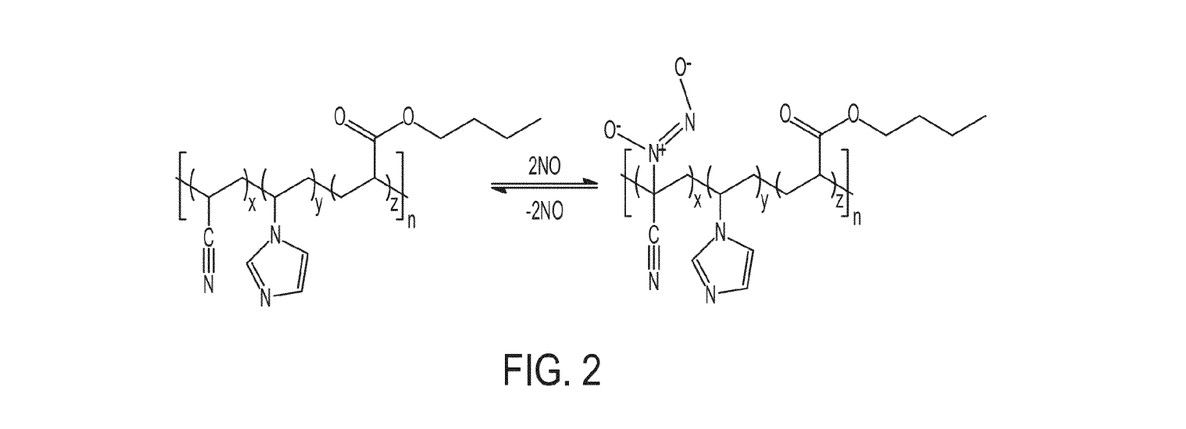
FIG. 2 shows the reversible binding and release of NO on an AN/VIM/BA terpolymer composition in accordance with an embodiment of the invention.

FIG. 1 shows the reversible reaction of NO with AN/VIM to form the diazeniumdiolate functional group. FIG. 2 shows the reversible binding of NO to AN/VIM/BA. It is believed that incorporation of the VIM comonomer to the copolymer and VIM, BA or IP to the terpolymer further enhances the α-hydrogen acidity in PAN. This same effect has been demonstrated in other AN-based polymers, such as AN/VIM/isoprene, AN/VIM/butyl acrylate, AN/VIM/ethylene, AN/VIM/butadiene, and AN/VIM/3,4-dimethoxystyrene. AN/VIM melt-spun fiber can successfully bind NO, and then allow release under humidity, thereby storing NO for release once used for dressing a wound as a suture.

Figure 5:
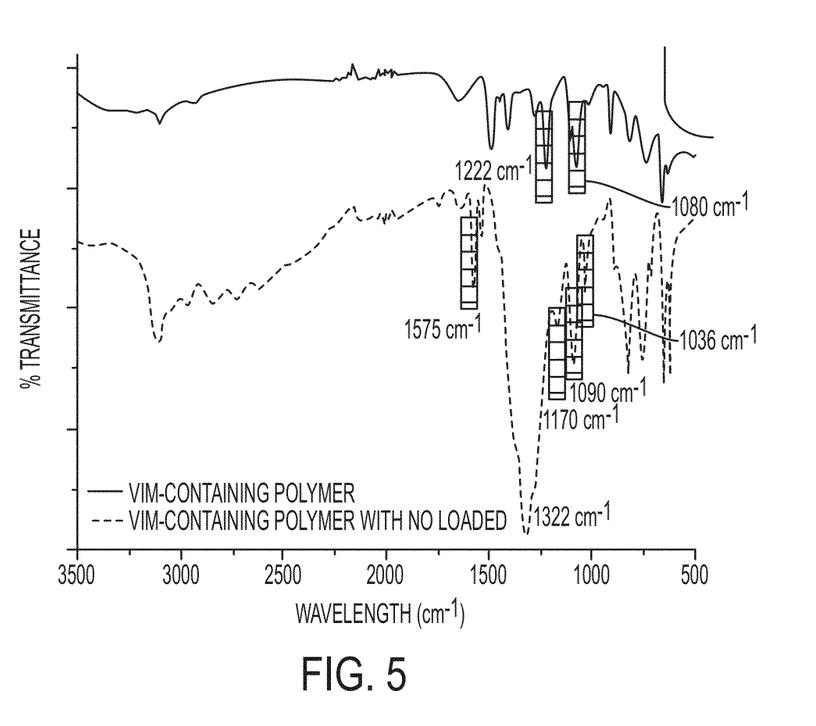
FIG. 5 shows the ATR spectra of a VIM-containing polymer in the presence and absence of NO, in accordance with an embodiment of the invention.

Although FIG. 1 shows the binding of the diazeniumdiolate functional group to the carbon backbone of the AN monomer in the claimed polymer, in certain embodiments of the invention, the diazeniumdiolate functional group can bind to the carbon backbone of the co-monomer (such as VIM or BA or IP) in the claimed polymer. FIG. 5 shows an ATR spectra of a VIM-containing polymer loaded with NO. The spectra demonstrates the binding of NO by a VIM-containing polymer by virtue of the change in the transmittance profile of the NO-loaded polymer relative to untreated polymer. This demonstrates that VIM monomer in a AN/VIM copolymer can bind NO in addition to binding of NO by the AN monomer in the AN/VIM copolymer.

The tensile strength of commercial sutures is in the range of 20-500 MPa. The tensile strength of NO-loaded AN/VIM melt-spun fiber is about 103 MPa, indicating that the melt-spun fiber is strong enough to be used as a suture.

After binding of NO, the polymer fibers retain their physical properties. They have extreme flexibility and durable. It is important that moisture be removed from the reaction chamber prior to NO loading on the fibers. When moisture is present, the fibers appear to swell upon reaction with NO. The diameter tripled in size, and after a week the fibers became brittle.

In certain embodiments of the invention, the polymers of the claimed invention comprise one or more biodegradable monomers. In certain embodiments, the biodegradable monomer is selected from caprolactam, lactide or glycolide.

In certain embodiments of the invention, lactide, glycolide, caprolactone, and other monomers are polymerized by ring-opening polymerization. Catalyst used in the reaction are either tin or zinc compounds. This polymer is bioabsorbable, and used to coat the surface of the NO releasing bandage to control release of NO. Polymer solutions used for coating are composed of 1 to 15% polymer by weight.

In certain embodiments of the invention, the polymer fibers are coated with a biodegradable polymer to control the release rate of NO. The coating materials are biodegradable polymers, including but not limited to polyglycolide, polylactide, polycaprolactone, poly (lactic-co-glycolide acid), poly (glycolide-co-caprolactone), and poly (glycolide-co-trimethylene carbonate). A non-porous coating is ideal to get a maximum delay of NO release from the melt-spun fiber. Dipping melt-spun AN/VIM NO loaded fibers into the 2% w/w PCL/CHCl$_3$ solution resulted in a porous coating that is distributed evenly along the entire fiber.

Figure 3A:
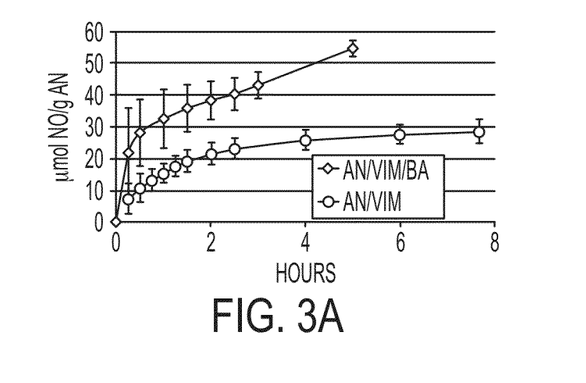
FIGS. 3A and 3B show a NO release profile comparison between a AN/VIM copolymer composition and a AN/VIM/BA terpolymer composition over a period of hours and days in accordance with an embodiment of the invention.
Figure 3B:
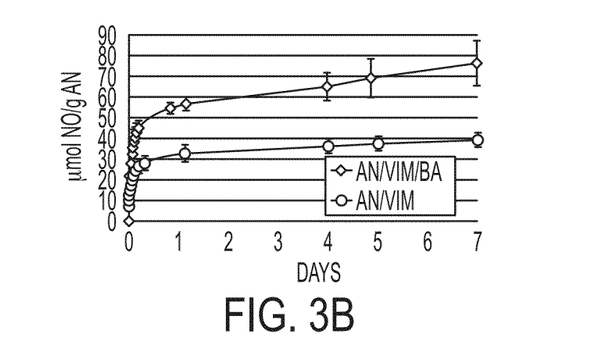

FIG. 3 shows the release profile of NO from electrospun AN/VIM/BA compared to AN/VIM. As humidified air passes over the NO loaded electrospun fiber, NO is released and quantified. The release profiles are normalized by weight to the percentage of AN monomers in the given polymer. In FIG. 3A, the initial rates of release are shown for the first hours of release. The release rate for AN/VIM/BA is faster than AN/VIM, and holds steady from hours 1 to 5. The release of AN/VIM begins to decrease after 2 hours. NO release from AN/VIM/BA begins to decrease at day 1, but holds steady throughout the 7 days. Over the 7 days, the AN/VIM/BA released up to 76 µmol NO/g AN. FIG. 3B shows AN/VIM release nearing a plateau at day 7, where the AN/VIM/BA holds a steady release. The greater release of NO can be attributed to the smaller fiber diameter of the AN/VIM/BA electrospun dressings. Diameter of the AN/VIM/BA is 175 nm, compared to the 657 nm diameters of the AN/VIM copolymer. The smaller fibers give more surface area of the dressing for NO binding, allowing for a greater capacity for storage and delivery of NO. The AN co/ter-polymer ratios for AN/VIM and AN/VIM/BA are about the same percentage of polymer composition, at 82 and 80 percent respectively.

Figure 4:
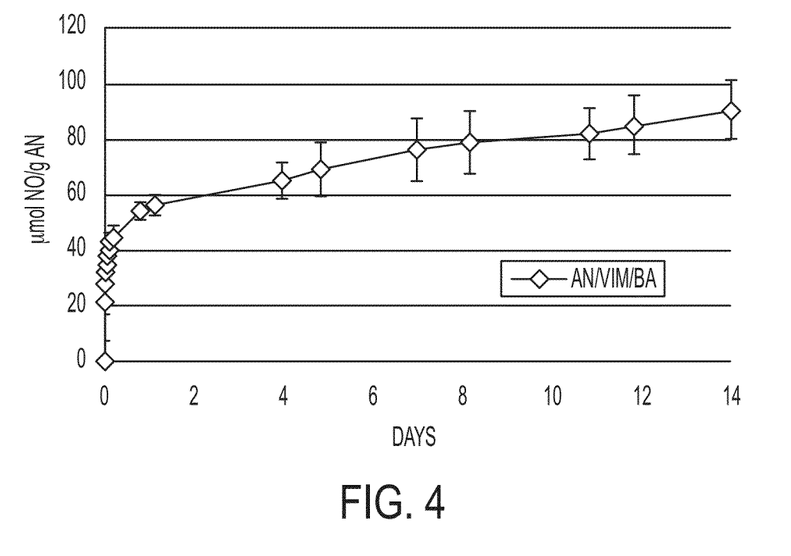
FIG. 4 shows a NO release profile from a AN/VIM/BA terpolymer composition over a period of 14 days in accordance with an embodiment of the invention.

In an embodiment of the invention, a bandage is prepared from fibers that comprise polymers of the claimed invention. As shown in FIG. 4, these bandages made from AN/VIM/BA polymers are capable of delivering up to 90 μmol NO/g AN over a period of 14 days.

Figure 6:
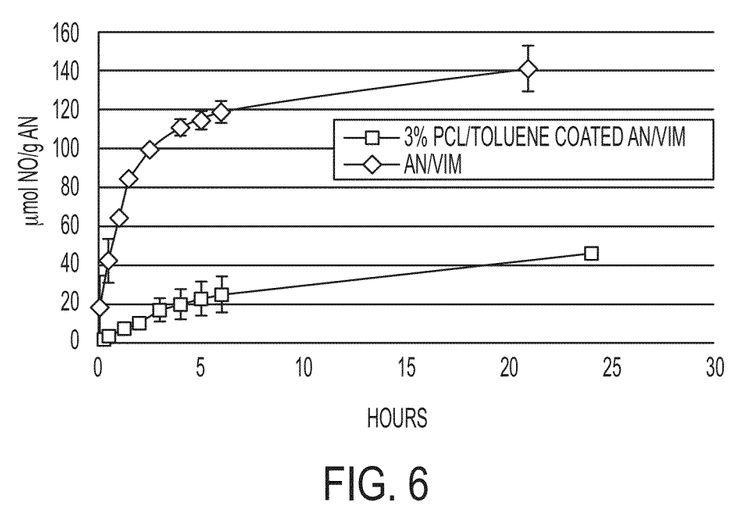
FIG. 6 shows a NO release profile comparison between a AN/VIM polymer composition with and without a biodegradable coating in accordance with an embodiment of the invention.

FIG. 6 shows a NO release profile comparison between a AN/VIM polymer composition with and without a biodegradable coating. For wound healing applications, it is desirable to have a delay in NO release of approximately 12-24 hours. A small amount of NO may be released to prevent infection, but a longer release period is needed for enhanced wound healing effects. By using a biodegradable coating, the release of NO can be delayed and controlled, depending on the purpose of application. Coatings can be composed of polylactic acid (PLA), polycaprolactone (PCL), polyethylene oxide (PEO), or other biodegradable monomers. The coated fibers in FIG. 6 are coated with a 3% w/w solution of polycaprolactone (PCL) in toluene. NO loaded AN/VIM sutures are dipped in the coating solution and allowed to dry. The uncoated sutures release approximately 140 μmol NO/g AN in one day. The PCL coated AN/VIM sutures release approximately 46 μmol NO/g AN in one day. The coated fiber shows a significant delay in the release of NO from the AN/VIM suture.

Figure 7A:
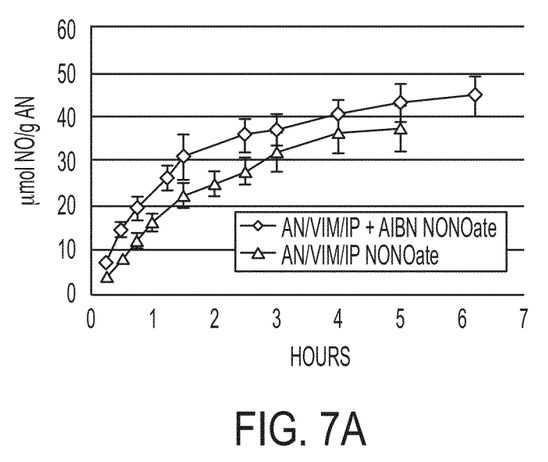
FIGS. 7A and 7B show a NO release profile comparison between a AN/VIM/IP terpolymer composition and a AN/VIM/IP terpolymer composition crosslinked with AIBN over a period of hours and days in accordance with an embodiment of the invention.
Figure 7B:
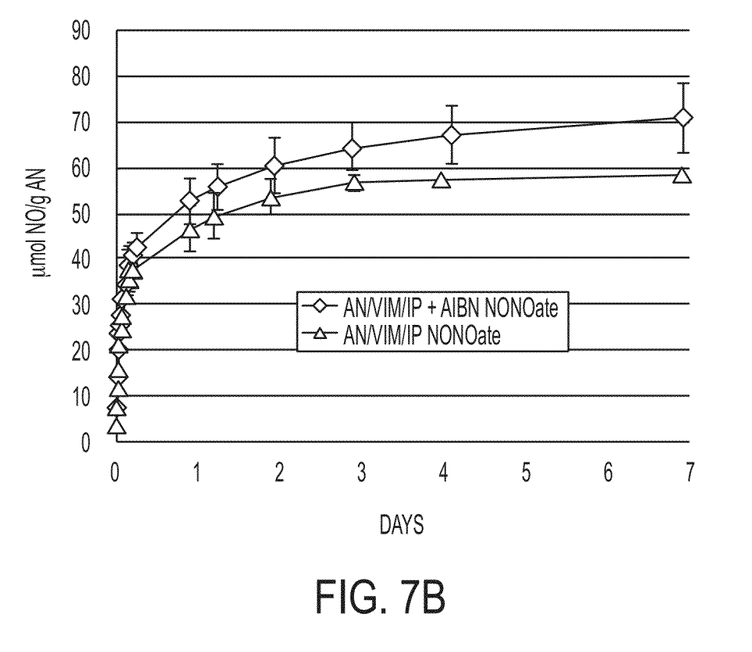

FIGS. 7A and 7B show a NO release profile comparison between a AN/VIM/IP terpolymer composition and a AN/VIM/IP terpolymer composition crosslinked with AIBN over a period of hours and days. The release profiles were determined at a temperature of 37° C. and 85% relative humidity. The AIBN cross-linked terpolymer composition releases more NO than the un-crosslinked composition at a rate of between 10 to 45 μmol NO/g AN over a period of 7 hours (FIG. 7A), and at a sustained rate of between 40 to 70 μmol NO/g AN over a 7 day period (FIG. 7B).

In certain embodiments of the invention, the total release of the coated AN/VIM suture reaches the total release of the uncoated suture over the course of several days. It is desirable to prolong the release of NO from sutures because they typically remain in place for several days when in use.

The following examples further illustrate the invention; however, the examples should not be construed as in any way limiting its scope.

The polymerization of a AN/VIM solution was performed in a 250 mL flask fitted with a thermocouple probe, condenser, addition funnel and nitrogen inlet. After charging the flask with DMF, it was purged with nitrogen for 30 min. The monomers, AIBN and 1-dodecanethiol were added drop wise into the flask for 5 h. AN/VIM was used in a molar ratio of 82/18. The polymerization was carried out at 70° C. with continuous stirring. The AN/VIM copolymer was precipitated in de-ionized water, then filtered and washed with methanol and hexane. Finally, it was dried in a vacuum oven for two days until a constant weight was obtained.

The polymerization of a AN, VIM and BA solution was carried out in a 250 mL flask fitted with a thermocouple probe, condenser, addition funnel and nitrogen inlet. The flask was charged with 50 mL DMF. Then the monomers: AN (24.64 g, 0.464 moles), VIM (2.156 g, 0.022 moles.), BA (4.000 g, 0.031 moles), the initiator AIBN (0.124 g, 0.00075 moles) and the chain transfer agent, 1-dodecanethiol (0.0080 g) were dissolved in 30 mL of DMF and added drop wise into the flask over a period of 15-20 min. The polymerization reaction was carried out at 71° C. with continuous stirring (280 rpm) for 16 hrs. De-ionized water was used to precipitate the terpolymer. The terpolymer is then filtered and washed with methanol and hexane to remove residual monomers and dried afterwards in vacuum oven for 24 hrs.

In certain embodiments of the invention, the AN-containing polymers are made into fibers by use of electrospinning. In other embodiments, the AN-containing polymers are made into fibers by melt spinning using known techniques.

In certain embodiments, the AN-based polymers are made into non-woven fiber mats by use of electrospinning. A solution in the range of 15-30% weight/volume, but preferably 24% weight/volume, is made by stirring at room temperature. The solution is then loaded into a syringe with a spinneret with a needle gauge of 18 to 22. A voltage in the range of 8-20 kV, but preferably 15 kV, is applied to the spinneret. The fibers are collected on a rotating drum which spins from 0-5000 rpm, but preferably 200 rpm.

A 0.0050 g sample of a AN-containing polymer was placed in pressure chamber. Moisture was removed from chamber by purging with Nitrogen for 30 minutes. Nitric oxide was pumped into chamber to react with copolymer and held at a constant pressure of 4 atm for 60 minutes at room temperature. After evacuation of NO from chamber, fibers were purged under Nitrogen for 60 minutes to remove excess NO.

NO loaded fibers were coated using a 1% to 3% PCL/Toluene solution. Using a glass stirring rod, a light coating was rolled over each side of the fibers. This gives a uniform coating on the fibers that is approximately 25 nm thick.

Fiber sample was held in sample chamber, and NO was released under controlled humidity environment. Nitrogen passes through a flask containing a saturated potassium chloride solution, which maintains a relative humidity of about 85%. The Nitrogen flow carries moisture through the sample chamber to release NO from the fiber sample. The air flow then carries NO to a vial containing 15 mL of deionized water, and is bubbled into the solution to produce nitrite ions. Samples, drawn at predetermined intervals, are tested with Griess Reagent for presence of nitrite ions. This testing is done with 0.10 mL nitrite containing sample, 0.10 mL Griess Reagent, and 2.80 mL deionized water. Solution is allowed to react with nitrite ions for 30 minutes, resulting in the formation of an azo dye which is a pink solution. To quantify dissolved NO, a UV absorption is taken at a wavelength of 525 nm against a blank solution of Griess reagent (0.10 mL Griess reagent and 2.90 mL deionized water).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments will become apparent to those of ordinary skill in the art upon reading the foregoing description. Accordingly, this invention includes all modifications and equivalents of the subject matter recited in the claims appended hereto.

What is claimed is:

1. A nitric oxide-releasing acrylonitrile-based polymer, wherein the polymer is a copolymer of acrylonitrile and at least one olefinic monomer that contains a >C=C<group, wherein the copolymer comprises at least one nitric oxide releasing group, and wherein the nitric oxide releasing group is bound to the olefinic monomer within the polymer.

2. The polymer of claim 1, wherein the olefinic monomer is 1-vinyl imidazole.

3. The polymer of claim 1, wherein the copolymer further comprises a second comonomer.

4. The polymer of claim 3, wherein the second comonomer is 4-vinyl imidazole, 2-vinyl imidazole, 1-methyl-2-vinyl imidazole; acrylate, methyl acrylate, ethyl acrylate, butyl acrylate, methacrylate, methyl methacrylate, butyl methacrylate, acrylic hydroxyl, methacrylic hydroxyl, diene, isoprene, butadiene, ethylene and propylene.

5. The polymer of claim 1, wherein the copolymer comprises a biodegradable monomer.

6. The polymer of claim 5, wherein the biodegradable monomer is caprolactam, lactide or glycolide.

7. A composition comprising fibers, wherein the fibers are made from nitric oxide-releasing acrylonitrile-based polymer, wherein the polymer is a copolymer of acrylonitrile and at least one olefinic monomer that contains a >C=C<group, wherein the copolymer comprises at least one nitric oxide releasing group, and wherein the nitric oxide releasing group is bound to the olefinic monomer within the polymer.

8. The composition of claim 7, wherein the fibers are electrospun or melt spun fibers.

9. The composition of claim 7, wherein the fibers further comprise a coated polymer layer.

10. The composition of claim 9, wherein the polymer layer comprises a biodegradable polymer.

11. The composition of claim 10, wherein the biodegradable polymer is polyglycolide, polylactide, polycaprolactone, poly (lactic-co-glycolide acid), poly (glycolide-co-caprolactone), and poly (glycolide-co-trimethylene carbonate).

12. A medical device comprising the polymer of claim 1.

13. The medical device of claim 12, wherein the medical device is a suture.

14. The medical device of claim 12, wherein the medical device is a bandage.

15. The medical device of claim 12, wherein the medical device is a textile fabric.

16. The medical device of claim 13, wherein the suture is a braided suture.

* * * * *